United States Patent [19]

Doi

[11] Patent Number: 4,876,331
[45] Date of Patent: Oct. 24, 1989

[54] COPOLYESTER AND PROCESS FOR PRODUCING THE SAME

[75] Inventor: Yoshiharu Doi, Yokohama, Japan

[73] Assignee: Mitsubishi Kasei Corporation, Tokyo, Japan

[21] Appl. No.: 230,461

[22] Filed: Aug. 10, 1988

[30] Foreign Application Priority Data

| Aug. 18, 1987 | [JP] | Japan | 62-204537 |
| Aug. 18, 1987 | [JP] | Japan | 62-204538 |
| Dec. 15, 1987 | [JP] | Japan | 62-316446 |
| Mar. 2, 1988 | [JP] | Japan | 63-49015 |
| Jul. 18, 1988 | [JP] | Japan | 63-178448 |

[51] Int. Cl.$^4$ ............... C08G 63/02; C08H 5/00
[52] U.S. Cl. ................................ 528/361; 530/200
[58] Field of Search ............ 528/361, 354; 260/97, 260/107

[56] References Cited

U.S. PATENT DOCUMENTS

| 4,358,583 | 11/1982 | Walker et al. | 528/361 X |
| 4,477,654 | 10/1984 | Holmes et al. | 528/361 |
| 4,562,245 | 12/1985 | Stageman | 528/361 |

FOREIGN PATENT DOCUMENTS

| 56-86930  | 7/1981  | Japan . |
| 56-117793 | 9/1981  | Japan . |
| 57-74084  | 5/1982  | Japan . |
| 57-150393 | 9/1982  | Japan . |
| 58-69224  | 4/1983  | Japan . |
| 59-220192 | 12/1984 | Japan . |
| 60-199392 | 10/1985 | Japan . |
| 60-214888 | 10/1985 | Japan . |
| 60-251889 | 12/1985 | Japan . |
| 61-293385 | 12/1986 | Japan . |
| 62-55094  | 3/1987  | Japan . |

OTHER PUBLICATIONS

S. Shimizu and T. Suzuki, Hakko to Kagyo, 45(11), 1080, (1987), "Production of Poly-Beta-Hydroxybutyric Acid from Methanol by Microorganisms".
Appl. Microbiol, Biotechnol, 27, 487, (1988).
Polymer Journal, 19(11), 1241, (1987).
Polymer Communications, 29, 112, (1988).
Macromolecules, 20, 3086, (1987).
Chemical Week, Aug. 28, 55, (1985).

Primary Examiner—Earl Nielsen
Attorney, Agent, or Firm—Linda M. Buckley; David G. Conlin

[57] ABSTRACT

According to the present invention, a novel copolyester comprising 3-hydroxybutyrate unit, 3-hydroxyvalerate unit and 5-hydroxyvalerate unit; 3-hydroxybutyrate unit and 4-hydroxybutyrate unit; or 3-hydroxybutyrate unit, 4-hydroxybutyrate unit and 3-hydroxyvalerate unit is easily obtained.

Further, since the copolyester according to the present invention has various excellent specific properties, it is extremely suitable as the biomedical materials such as suture material and fixation materials for bone fracture, and its application to various fields such as the slow-releasing system, etc. is expected.

4 Claims, 9 Drawing Sheets

COPOLYESTER AND PROCESS FOR PRODUCING THE SAME

BACKGROUND OF THE INVENTION

The present invention relates to a copolyester comprising 3-hydroxybutyrate unit (hereinafter referred to as 3HB unit) and one selected from the group consisting of (1) 3-hydroxyvalerate unit (hereinafter referred to as 3HV unit) and 5-hydroxyvalerate unit (hereinafter referred to as 5HV unit), (2) 4-hydroxybutyrate unit (hereinafter referred to as 4HB unit) and (3) 4HB unit and 3HV unit, and also relates to a process for producing the above-mentioned copolyester. More in detail, the present invention relates to a novel copolyester comprising 3HB unit and one selected from the group consisting of (1) 3HV unit and 5HV unit, (2) 4-HB unit and (3) 4HB unit and 3HV unit, being produced by using a microorganism which can accumulate polyester therein, and to a process for producing the novel copolyester.

Since poly-3-hydroxybutyrate (hereinafter referred to as PHB) is a thermoplastic high polymer which is accumulated as the energy-storage substance in the cells of large number of microorganism and shows an excellent biodegradability and an excellent adaptability to living bodies, PHB has attracted one's attention as the "clean" plastic which meets the purpose of environmental protection, and its application to various fields, for example, biomedical material such as suture material and fixation materials for bone fracture and slow-releasing systems which slowly release medicines and agricultural chemicals has been expected for many years. Particularly in recent years, since synthetic plastics have come to present a severe social problems the environmental pollution and the circulation of the resources, PHB has attracted one's attention as a biopolymer which does not depend on petroleum.

However, since PHB is poor in impact strength due to its rigidity, it is unsuitable for practical uses, and from the reason of high cost for producing PHB, its industrial production has not been reduced to practice. Accordingly, in order to improve the impact strength of PHB, a proposal of producing a copolymer of 3-hydroxybutyrate has been raised.

For instance, in Japanese Patent Applications Laid-Open (KOKAI) Nos. 57-150393 (1982) and 59-220192 (1984), a copolymer comprising 3HB unit and 3HV unit has been disclosed. The process disclosed in these Applications is a process for producing the copolyester by propagating the microorganism in the former stage as in the conventional process for producing PHB and culturing the microorganism under the limitation of nitrogen and/or phosphorus in the later stage.

However, in the former Application (No. 57-150393 (1982)), there is a description that a copolyester comprising 99.5 to 50 mol% of 3HB unit and 0.1 to 50 mol% of another ester unit such as 3HV unit can be produced by using propionic acid and isobutyric acid as the substrate in the latter stage of culture. However, in this Application, only a copolyester containing at most 33 mol% of 3HV unit has been shown, and any copolyester containing 3HV unit more than 33 mol% has not been exactly shown.

On the other hand, in the latter Application (No. 59-220192 (1984)), there is a qualitative description that a copolyester comprising at least 40 mol% of 3HB unit and another ester unit is produced by using carbon from the cellular substance of the wasted microorganism after extracting PHB in the latter stage of culture. However, in this Application, no copolyester having an exact ratio of 3HB unit and 3HV unit has been described. Also, the process disclosed therein is complicated, and the composition of the cellular substance varies in the kind and the amount of the component according to the culture conditions. Namely the process is not practical.

Further, in the case where the content of 3HV unit in the copolyester increases from 0 to 33 mol%, it has been known that the melting point (Tm) of the copolyester is rapidly lowered from 180° C. to 85° C. [refer to T. L. Bluhm et al., Macromolecules, 19, 2871–2876 (1936)]. This dependency of the melting point on the content of 3HV unit means that it is difficult to industrially obtain product of equal quality.

As a result of the present inventor's studies on industrially profitable and easy method for producing a copolyester in which the molar content of other unit is relatively large compared with the molar content of 3HB unit, it has been found by the present inventor that a copolyester 3 in which the molar content of other units is relatively large compared with the molar content of 3HB unit is formed and accumulated in the microorganism when a microorganism having an ability of producing PHB is cultured in the latter stage, wherein nitrogen and/or phosphorus is limited, in the presence of a carbon source selected from the group consisting of (1) a compound represented by the following formula (I):

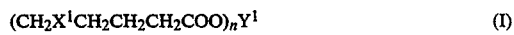

$$(CH_2X^1CH_2CH_2CH_2COO)_nY^1 \qquad (I)$$

wherein $X^1$ represents a hydroxyl group or a halogen atom, n represents an integer of 1 to 4 and $Y^1$ represents a hydrogen atom or a uni- to tetravalent metal atom, (2) a compound represented by the following formula (II);

$$(CH_2X^2CH_2CH_2COO)_nY^2 \qquad (II)$$

wherein $X^2$ represents a hydroxyl group or a halogen atom, n represents an integer of 1 to 4 and $Y^2$ represents a hydrogen atom or a uni- to tetravalent metal atom, (3) a compound represented by the above mentioned formula (II) and a compound represented by the following formula (III):

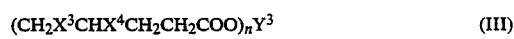

$$(CH_2X^3CHX^4CH_2CH_2COO)_nY^3 \qquad (III)$$

wherein $X^3$ represents a hydrogen atom, a halogen atom or a hydroxyl group, $X^4$ represents a hydrogen atom, a halogen atom, a hydroxyl group or an alkyl group, n represents an integer of 1 to 4 and $Y^3$ represents a hydrogen atom or uni- to tetravalent metal atom, (4) 1,4-butanediol and (5) γ-butyrolactone, and on the basis of the finding, the present invention has been attained.

SUMMARY OF THE INVENTION

In a first aspect of the present invention, there is provided a copolyester having an intrinsic viscosity in a range of 0.4 to 10.0 dl/g in chloroform at 30° C. and comprising 3-hydroxybutyrate unit and one selected from the group consisting of (1) 3-hydroxy-valerate unit and 5-hydroxyvalerate unit, (2) 4-hydroxybutyrate unit and (3) 4-hydroxybutyrate unit and 3-hydroxyvalerate unit.

In a second aspect of the present invention, there is provided a process for producing a copolyester comprising 3-hydroxybutyrate unit and one selected from the group consisting of (1) 3-hydroxyvalerate unit and 5-hydroxyvalerate unit, (2) 4-hydroxyvalerate unit and (3) 4-hydroxyvalerate unit and 3-hydroxyvalerate unit and having an intrinsic viscosity in the range of 0.4 to 10.0 dl/g in chloroform at 30° C. which process comprising the steps of propagating a microorganism having an ability of producing poly-3-hydroxybutyrate, and culturing said microorganism under a limitation of nitrogen and/or phosphorus and in the presence of a carbon source selected from the group consisting of (i) a compound represented by the formula (I);

$$(CH_2X^1CH_2CH_2CH_2COO)_nY^1 \quad (I)$$

wherein $X^1$ represents a hydroxyl group or a halogen atom, n represents an integer of 1 to 4 and $Y^1$ represents a hydrogen atom or a uni- to tetravalent metal atom, (ii) a compound represented by the formula (II):

$$(CH_2X^2CH_2CH_2COO)_nY^2 \quad (II)$$

wherein $X^2$ represents a hydroxyl group or a halogen atom, n represents an integer of 1 to 4 and $Y^2$ represents a hydrogen atom or a uni- to tetravalent metal atom, (iii) a compound represented by said formula (II) and a compound represented by the formula (III):

$$(CH_2X^3CHX^4CH_2CH_2COO)_nY^3 \quad (III)$$

wherein $X^3$ represents a hydrogen atom, a halogen atom or a hydroxyl group, $X^4$ represents a hydrogen atom, a halogen atom, a hydroxyl group or an alkyl group, n represents an integer of 1 to 4 and $Y^3$ represents a hydrogen atom or a uni- to tetravalent metal atom, (iv) 1,4-butanediol and (v) γ-butyrolactone, thereby forming and accumulating said copolyester in said microorganism.

BRIEF EXPLANATION OF THE DRAWINGS

Of the attached drawings.

Figure 1:
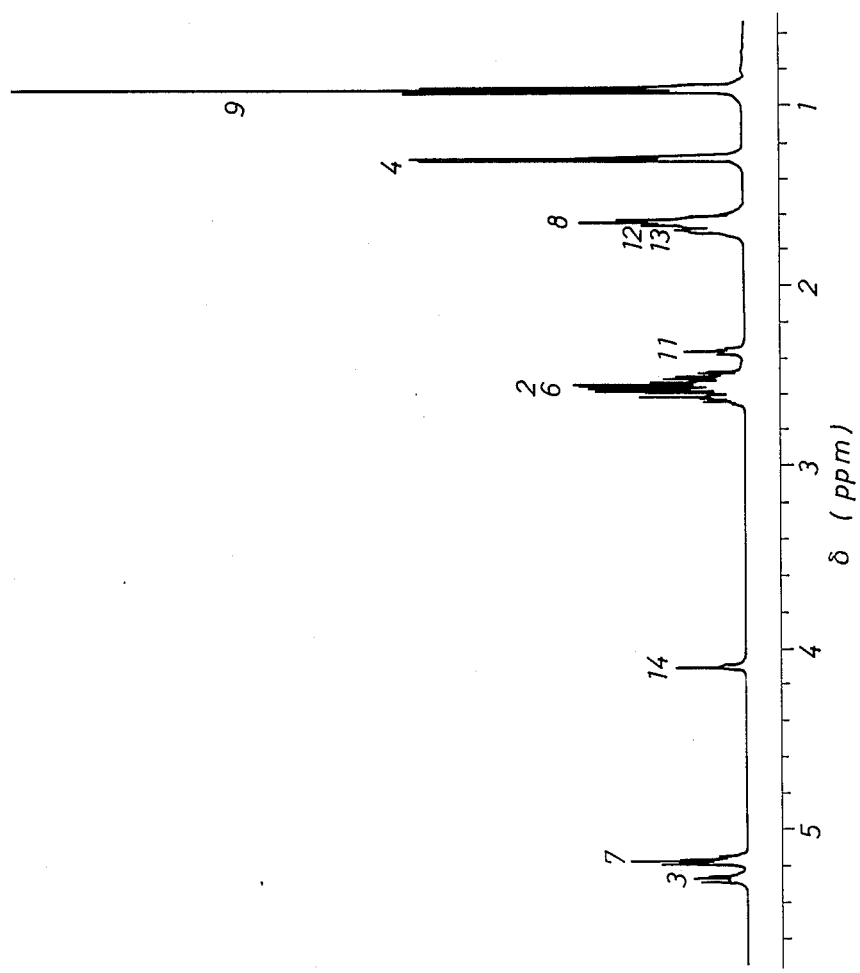
FIGS. 1, 3, 5 and 7 respectively show the $^1$H-NMR spectrum at 500 MHz of the copolyesters respectively obtained in Examples 2, 7, 16 and 21, and FIGS. 2, 4, 6 and 8 respectively show the $^{13}$C-NMR spectrum at 125 MHz of the copolyesters respectively obtained in Examples 2, 7, 16 and 21.
Figure 2:
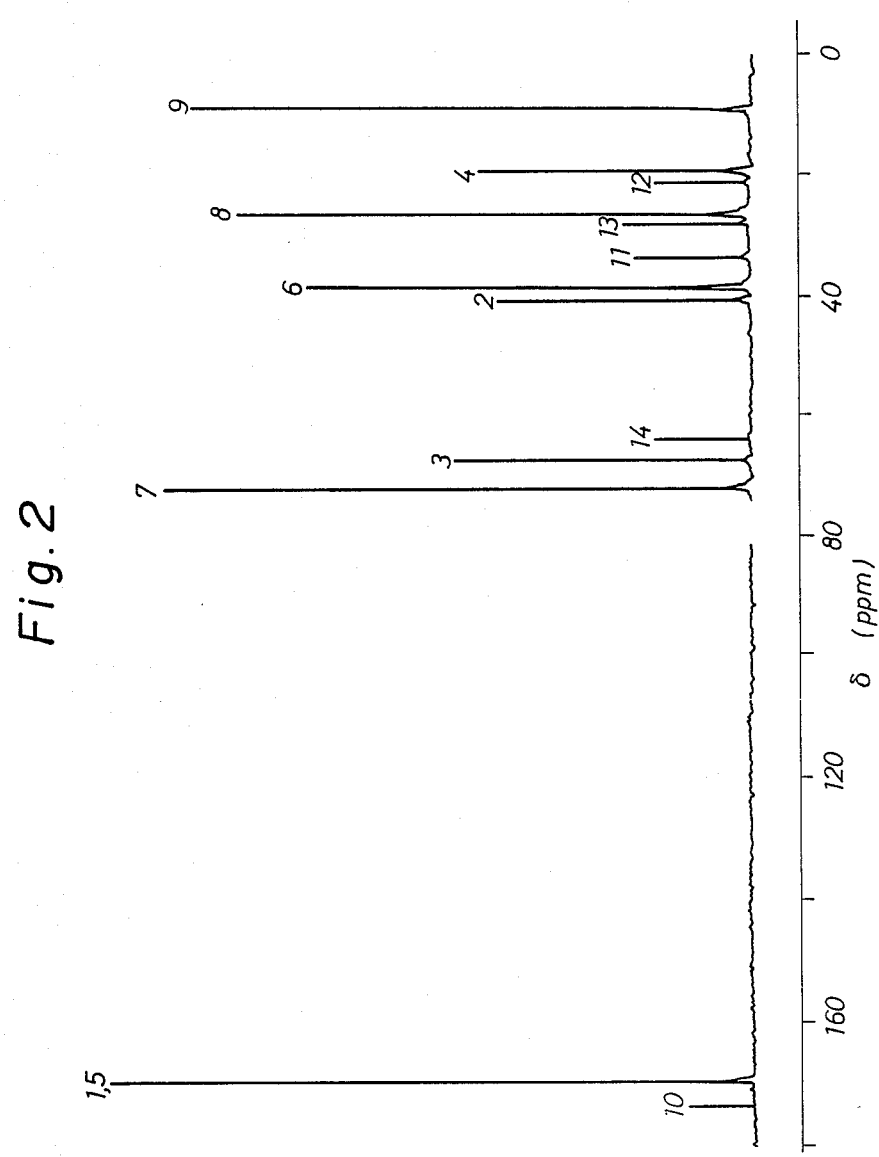

The numerical references attached to the peaks of FIGS. 1 to 4 corresponding respectively to the numerical references attached to the following formulae.

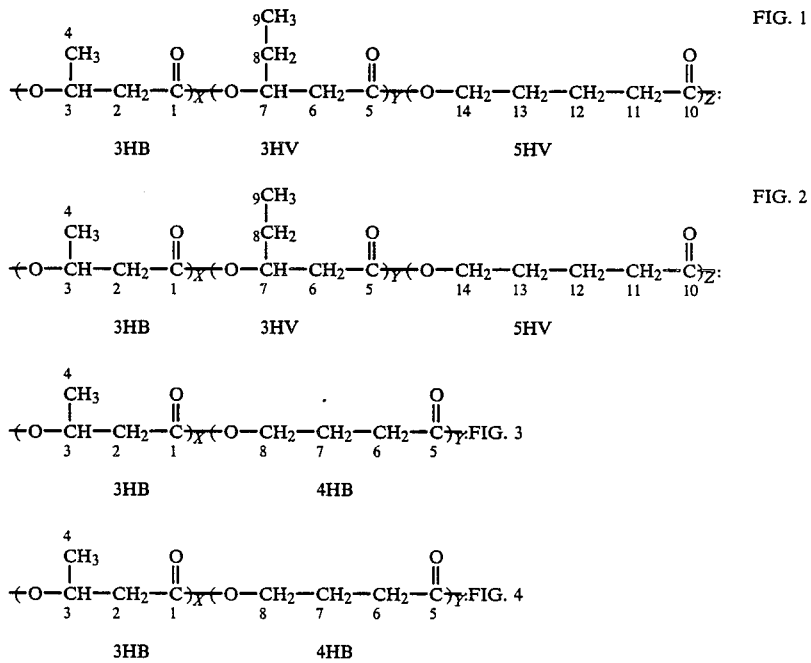

DETAILED DESCRIPTION OF THE INVENTION

3HB unit, 4HB unit, 3HV unit and 5HV unit contained in the copolyester according to the present invention are respectively represented by the following formulae:

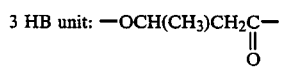

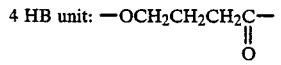

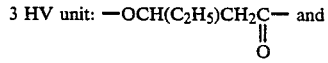

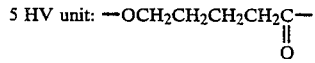

Although the microorganism used in the present invention is not particularly limited in the case where the microorganism has an ability of producing PHB, for the practical use, a microorganism belonging to the genus Alcaligenes such as *Alcaligenes faecalis, Alcaligenes ruh-*

*landii, Alcaligenes latus, Alcaligenes aquamarinus, Alcaligenes eutrophs,* etc. is preferably used.

As the representative examples of the strains belonging to the above species, *Alcaligenes faecalis* ATCC 8750, *Alcaligenes ruhlandii* ATCC 15749, *Alcaligenes latus* ATCC 29712, *Alcaligenes aquamarinus* ATCC 14400 and *Alcaligenes eutrophs* H-16 ATCC 17699, *Alcaligenes eutrophs* NCIB 11597 which is a mutant of the H-16 strain, *Alcaligenes eutrophs* NCIB 11598, *Alcaligenes eutrophs* NCIB 11599, *Alcaligenes eutrophs* NCIB 11600, etc. may be mentioned. Of these strains, *Alcaligenes eutrophs* H-16 ATCC 17699 and *Alcaligenes eutrophs* NCIB 11599 are particularly preferable in practical use.

The microbiological characteristics of these microorganism belonging to the genus Alcaligenes are described in, for instance, "BERGEY'S MANUAL OF DETERMINATIVE BACTERIOLOGY: Eight Edition, The Williams & Wilkins Company/Baltimore" and the microbilogical characteristics of *Alcaligenes eutrophs* H-16 is described in, for instance, "J. Gen. Microbiol., 115, 185–192 (1979)".

These microorganism are cultured by two stages as in the conventional process, namely the former stage of culture in which the microorganism is mainly propagated and the latter stage of culture in which the co-polyester is formed and accumulated in the microorganism under the limitation of nitrogen and/or phosphorus.

In the former stage of culture, the conventional culture process can be applied for the propagation of the microorganism. Namely, the culture medium and the culture conditions in and under which the microorganism can be propagated may be employed.

The component of the culture medium is not particularly limited if the components are the substances which can be used as the substrate by the microorganism. In the practical use, as the carbon source, for instance it is selected from the synthetic carbon sources such as methanol, ethanol, acetic acid, etc.; the inorganic carbon source such as carbon dioxide, etc.; natural substances such as yeast extract, molasses, peptone, meat extract, etc.; sugars such as arabinose, glucose, mannose, fructose, galactose, etc.; and sugar alcohols such as sorbitol, mannitol, inositol, etc. As the nitrogen source, for instance, it is selected from inorganic nitrogen compounds such as ammonia, ammonium salts, nitrates, etc.; and/or organic nitrogen compounds such as urea, corn steep liquor, casein, peptone, yeast extract, meat extract, etc. As the inorganic component, for instance, it is selected from calcium salts, magnesium salts, potassium salts, sodium salts, phosphates, manganese salts, zinc salts, iron salts, copper salts, molybdenum salts, cobalt salts, nickel salts, chromium salts, boron compounds, iodine compounds, etc.

Further, as occasion demands, vitamins may be used.

As the culture conditions, the culture temperature is, for instance, in the range of 20° to 40° C., preferably in the range of 25° to 35° C. and the pH of the culture medium is in the range of 6 to 10, preferably in the range of 6.5 to 9.5. The culture is carried out aerobically under this conditions.

In the case where the culture is carried out under different conditions from the above conditions, although the propagation of the microorganism becomes relatively insufficient, the culture may be carried out under such different conditions, if the microorganism is practically propagated.

The mode of culture may be in either the batch culture or the continuous culture.

The microorganism propagated in the former stage of culture are further cultured under the condition of limiting nitrogen and/or phosphorus.

Namely, the microorganisms are separated and collected from the culture liquid of the former stage of culture by a conventional liquid-solid separation technique such as filtration and centrifugation, and the thus collected microorganisms are subjected to the latter stage of culture. Instead of the above method, a method in which nitrogen phosphorus or the both are substantially exhausted after the former stage of culture and the culture liquid is subjected to the latter stage of culture without separating and collecting the microorganisms may be also employed.

In the latter stage of culture, the procedures are not necessarily different from the procedures in the former stage of culture except for containing substantially no nitrogen and/or phosphorus in the culture medium or the culture liquid and including a carbon source selected from the group consisting of (1) a compound represented by the formula (I), (2) a compound reprresented by the formula (II), (3) a compound represented by the formula (II) and a compound represented by the formula (III), (4) 1,4-butanediol and (5) γ-butyrolactone.

In the formula (I), $X^1$ represents a hydroxyl group or a halogen atom. As the halogen atom, a chlorine atom or a bromine atom is preferred. $Y^1$ represents a hydrogen atom, a univalent metal atom such as sodium and, potassium, a divalent metal atom such as calcium and magnesium, a trivalent metal atom such as aluminum, or a tetravalent metal atom. Among these metals, uni- to trivalent metal atoms are preferred. Further, n represents an integer of 1 to 4. As the compound represented by the formula (I), 5-chlorovaleric acid, 5-hydroxyvaleric acid, a sodium salt thereof, a potassium salt thereof, a calcium salt thereof, etc. may be mentioned.

In the formula (II), $X^2$ represents a hydroxyl group or a halogen atom. As the halogen atom, a chlorine atom or a bromine atom is preferred. $Y^2$ represents a hydrogen atom, a univalent metal atom such as sodium and potassium, a divalent metal atom such as calcium and magnesium, a trivalent metal atom such as aluminum, or a tetravalent metal atom. Among these metals, uni- to trivalent metal atoms are preferred. Furter n represents an integer of 1 to 4.

As the compound represented by the formula (II), derivatives of butyric acid such as 4-hydroxybutyric acid, 4-chlorobutyric acid, 4-bromobutyric acid, etc., a sodium salt thereof, a potassium salt thereof, a magnesium salt thereof, a calcium salt thereof, an aluminum salt thereof, etc. may be mentioned.

In the formula (III), $X^3$ represents a hydrogen atom, a hydroxyl group or a halogen atom. As the halogen atom, a chlorine atom and a bromine atom are preferred. $X^4$ represents a hydrogen atom, a halogen atom, preferably a chlorine atom or a bromine atom, a hydroxyl group or an alkyl group, preferably an alkyl group of 1 to 3 carbon atoms. $Y^3$ represents a hydrogen atom, a univalent metal atom such as sodium and potassium, a divalent metal atom such as calcium and magnesium, a trivalent metal atom such as aluminum, or a tetravalent metal atom. Further, n represents an integer of 1 to 4.

As the compound represented by the formula (III), valeric acid, 4-chlorovaleric acid, 4-hydroxyvaleric acid, 4-methylvaleric acid, 4-ethylvaleric acid, 5- hydroxyvaleric acid, 5-chlorovaleric acid, sodium salts thereof and potassium salts thereof may be mentioned.

The compound represented by the formula (I), the compound represented the formula (II), a mixture of the compound represented by the formula (II) and the compound represented by the formula (III), 1,4-butanediol or γ-butyrolactone is contained in the culture medium or the culture liquid in the latter stage of culture. In the latter case, the above substances may be contained at any stage in the latter stage of culture from the beginning to the end of culture, however, the substance is preferably contained at the beginning of the later stage of culture.

The compound represented by the formula (I) or (II), or 1,4-butandiol may be used in an amount which can form the aimed copolyester and does not hinder the growth of the microorganisms. Although the amount depends on the kind of strain of the microorganism used and the ratio (molar ratio) of the constitutional unit in the aimed copolyester, it is generally suitable that the above compound is contained at the amount of 3 to 40 g, preferably 5 to 30 g in one liter of the culture medium or the culture liquid.

In the case of using the compound represented by the formula (II) together with the compound represented by the formula (III), the total amount of the compounds is preferably 3 to 40 g, more preferably 5 to 30 g in one liter of the culture medium or the culture liquid. Further, the ratio (weight ratio) of the compound represented by the formula (II) is preferably 30 to 95%, more preferably 35 to 90%, and the ratio of the compound represented by the formula (III) is preferably 5 to 70%, more preferably 10 to 65%.

In the case of using γ-butyrolactone, the amount of γ-butyrolactone is preferably 3 to 100 g, more preferably 5 to 90 g in one liter of the culture medium or the culture liquid.

In the latter stage of culture, only the compound represented by the formula (I), the compound represented by the formula (II) a mixture of the compounds represented by the formulae (II) and (III), 1,4-butanediol or γ-lactone may be used as the carbon source, however, another carbon source which can be used as the substrate by the microorganism, for instance, glucose, fructose, methanol, ethanol, acetic acid, propionic acid, n-butyric acid, lactic acid, valeric acid and a salt of these acids can be used together. For instance, in the case of using glucose, the amount of glucose is at most 1.5 liter.

In the case of using γ-butyrolactone, 4-hydroxybutyric acid, a salt thereof and a diol such as 1,4-butanediol may be used together with γ-butyrolactone.

From the culture liquid or the culture medium thus obtained by the above culture, the microorganisms are separated and collected by the conventional liquid-solid separation technique such as filtration and centrifugation, and the thus collected microorganisms are washed and dried to obtain the dried fungus. From the thus dried fungus, the copolyester formed therein is extracted by a known method, for instance, extraction with an organic solvent such as chloroform. The copolyester is precipitated by adding a poor solvent, for instance, hexane to the thus obtained extract. Then, the copolyester according to the present invention having an intrinsic viscosity [η] of 0.4 to 10.0 dl/g in chloroform at 30° C. can be obtained by the ordinary method for separation.

According to the process for production of a copolyester of the present invention, in the case where the compound represented by the formula (I) is used in the latter stage of culture, a copolyester comprising 2 to 50 mol% preferably 10 to 40 mol% of 3HB unit, 3 to 95 mol%, preferably 10 to 90 mol% of 3HV unit and 3 to 90 mol%, preferably 5 to 80 mol% of 5HV unit can be obtained.

In the case where the compound represented by the formula (II), 1,4-butanediol or γ-butyrolactone is used, a copolyester comprising 40 to 97 mol%, preferably 50 to 95 mol% of 3HB unit and 3 to 60 mol%, preferably 5 to 50 mol% of 4HB unit can be obtained.

In the case where the compound represented by the formula (II) is used together with the compound represented by the formula (III), a copolyester comprising 10 to 90 mol%, preferably 10 to 80 mol% of 3HB unit, 3 to 60 mol%, preferably 3 to 50 mol% of 4HB unit and 5 to 87 mol%, preferably 10 to 70 mol% of 3HV unit can be obtained.

Particularly in the case where the ratio of 3HB unit in the copolyester of the present invention is not larger than 50 mol%, the stability of the melting temperature thereof becomes larger and the crystallizaton degree thereof becomes smaller. Accordingly, the copolyester becomes excellent in strength and the forming thereof such as spinning and rolling thereof becomes easier and stabilized, and the thus obtained formed products such as fibers and films are flexible and tough.

The present invention will be explained more precisely while referring to the following non-limitative Examples.

EXAMPLES 1 TO 3 AND COMPARATIVE EXAMPLE 1

Copolyesters were produced by using *Alcaligenes eutrophs* NCIB 11599 as follows.

Former stage of culture

The microorganism was cultured in the culture medium having the following composition for 24 hours at 30° C., and the microorganisms were separated from the culture liquid at the termination of the logarithmic propagation phase by centrifugation.

| Composition of the culture medium | |
|---|---|
| Yeast extract 10 g | Polypeptone 10 g |
| Meat extract 5 g | (NH$_4$)$_2$SO$_4$ 5 g |

The above substances were dissolved in one liter of de-ionized water, and the pH of the solution was adjusted to 7.0.

Latter stage of culture

The microorganisms obtained in the former stage of culture were suspended in the culture medium having the following composition at a rate of 5 g/liter and were cultured for 48 hours at 30° C.

From the thus obtained culture liquid, the microorganisms were separated by centrifugation.

Composition of the culture medium 0.5M aqueous solution of potassium dihydrogenphosphate 39.0 ml 0.5M aqueous solution of dipotassium dihydrogenphosphate 53.6 ml 20 Wt/V% aqueous solution of magnesium sulfate 1.0 ml
Carbon source*
A mineral solution**
*As the carbon source, 5-chlorovaleric acid and valeric acid were used (unit: g/liter of medium) as has been shown in TABLE 1. Further, in COMPARATIVE EXAMPLE 1, 20 g of butyric acid were used.
**A mineral solution

| | | |
|---|---|---|
| CoCl$_2$ | 119.0 mg | |
| FeCl$_3$ | 9.7 g | |
| CaCl$_2$ | 7.8 g | |
| NiCl$_2$ | 118.0 mg | |
| CrCl$_2$ | 62.2 mg | |
| CaSO$_4$ | 156.4 mg | |

These salts were dissolved in one liter of 0.1N hydrogen chloride.

Treatment of the microorganism

The microorganisms obtained by the latter stage of culture were washed with distilled water and acetone, and then, dried under a reduced pressure (at 20° C. under 0.1 mmHg) to obtain the dried fungus.

Separation and collection of the copolyester

The copolyester was extracted from the thus obtained, dried fungus with hot chloroform, and hexane was added to the thus obtained extract to precipitate the copolyester. The precipitate was collected by filtration and dried to obtain the copolyester.

Properties of the copolyester

The composition, the intrinsic viscosity, the melting temperature and the heat of fusion of the thus obtained copolyester were measured as follows:
Composition: by $^1$H-NMR at 500 MHz
Intrinsic viscosity [η]: in chloroform at 30° C.
Melting temperature Tm: according to DSC determination at a rate of temperature raise of 10° C./min
Heat of fusion ΔH: according to DSC determination The results are shown in TABLE 1.
Further, the $^1$H-NMR spectrum at 500 MHz of the copolyester obtained in EXAMPLE 2 was shown in FIG. 1, and the $^{13}$C-NMR spectrum at 125 MHz of the same was shown in FIG. 2.

TABLE 1

| | Carbon source (g) | | Weight of dried fungus (g) | Content of copolyester (%) | Composition of copolyester (mol %) | | | [η] (dl/g) | Melting temperature (°C.) | Heat of fusion (cal/g) |
|---|---|---|---|---|---|---|---|---|---|---|
| | 5-chloro valeric acid | valeric acid | | | [3 HB] | [3 HV] | [5 HV] | | | |
| Example 1 | 20 | 0 | 4.7 | 1 | 24 | 24 | 52 | — | — | — |
| Example 2 | 10 | 10 | 4.4 | 8 | 26 | 63 | 11 | 3.1 | 101 | 11.2 |
| Example 3 | 5 | 15 | 4.2 | 19 | 26 | 65 | 9 | 5.0 | — | — |
| Comparative Example 1 | — | — | 9.4 | 51 | 100 | 0 | 0 | 3.3 | 177 | 19.5 |

EXAMPLES 4 TO 12 AND COMPARATIVE EXAMPLE 2

The copolyesters were obtained as in EXAMPLE 1 except for using *Alcaligenes eutrophs* H-16 ATCC 17699 and respectively using the compounds shown in TABLE 2 as the carbon source in the latter stage of culture. The composition and the intrinsic viscosity of the thus obtained copolyesters were measured as in EXAMPLE 1, and the results are shown in TABLE 2.

Figure 3:
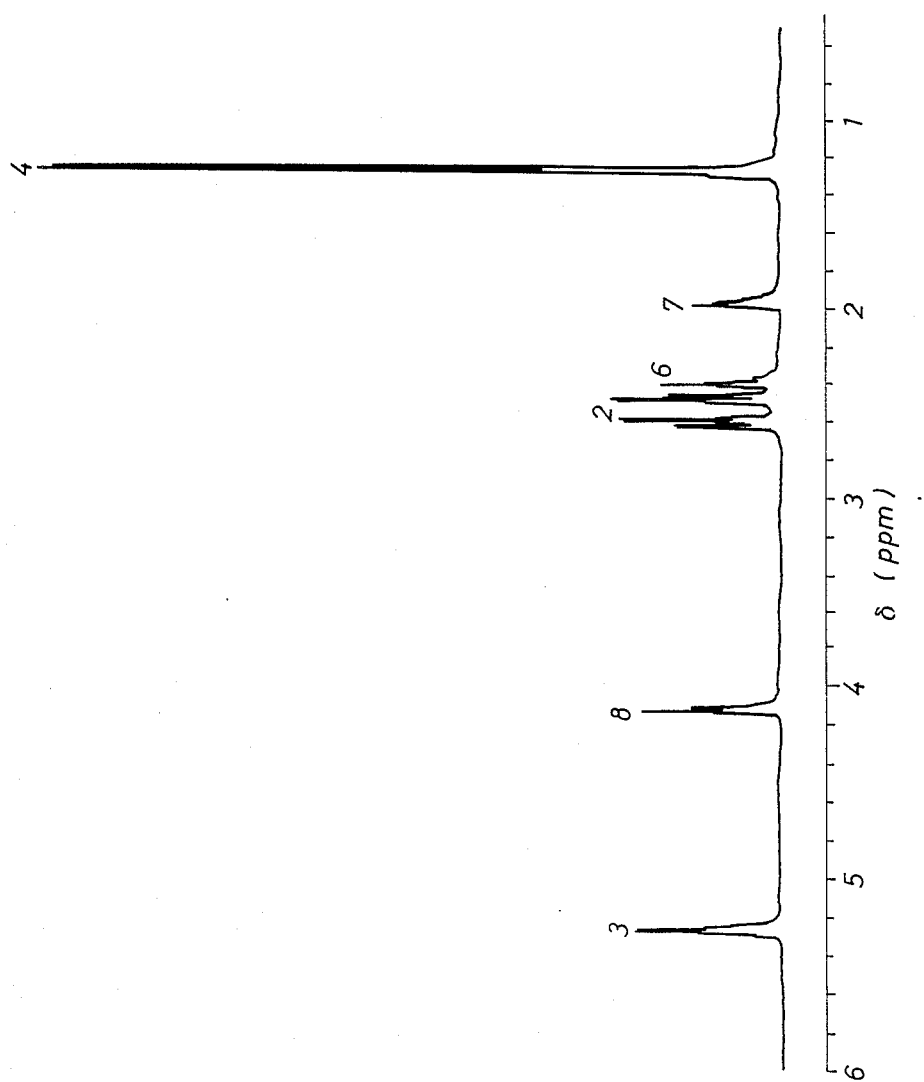
Figure 4:
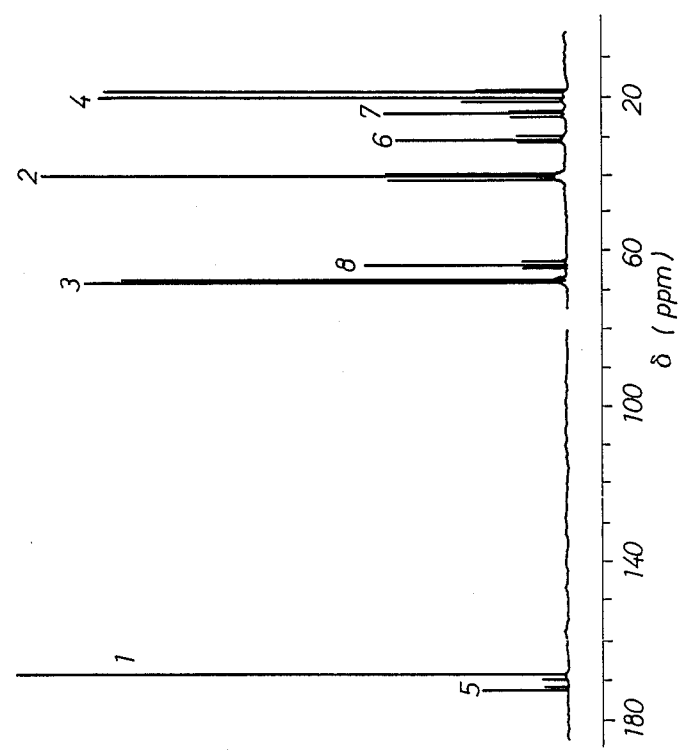

Further, the $^1$H-NMR spectrum at 500 MHz of the copolyester obtained in EXAMPLE 7 was shown in FIG. 3 and the $^{13}$C-NMR spectrum at 125 MHz of the same was shown in FIG. 4.

TABLE 2

| | Carbon source (g) | | Weight of dried fungus (g) | Content of copolyester (%) | Composition of copolyester (mol %) | | [η] (dl/g) |
|---|---|---|---|---|---|---|---|
| | 4-hydroxy butyric acid | butyric acid | | | 3 HB | 4 HB | |
| Example 4 | 4 | 0 | 2.8 | 7 | 75 | 25 | — |
| Example 5 | 8 | 0 | 3.3 | 14 | 74 | 26 | — |
| Example 6 | 12 | 0 | 4.1 | 18 | 74 | 26 | — |
| Example 7 | 16 | 0 | 3.5 | 19 | 73 | 27 | 4.3 |
| Example 8 | 20 | 0 | 2.9 | 19 | 69 | 31 | — |
| Example 9 | 24 | 0 | 3.5 | 13 | 66 | 34 | 4.0 |
| Example 10 | 28 | 0 | 3.5 | 8 | 64 | 36 | — |
| Example 11 | 4 | 15 | 8.5 | 53 | 95 | 5 | — |
| Example 12 | 8 | 10 | 7.6 | 48 | 87 | 13 | 3.9 |
| Comparative Example 2 | 0 | 20 | 9.6 | 51 | 100 | 0 | 3.3 |

EXAMPLE 13

The results of the copolyester obtained by the same procedures as in EXAMPLE 4 except for using 4-chlorobutyric acid (18 g/liter) as the carbon source in the latter stage of culture are shown in TABLE 3.
Of the data in TABLE 3, the chain distribution, the melting temperature and the heat of fusion of the copolyester were measured as follows:
Chain distribution; estimated from the multiplet resonance structure of the carbonyl carbon according to the method of the present inventor et al. (Y. Doi et al., Macromolecules, 19, 2860-2864 (1986))
Melting temperature; according to DSC determination (at a rate of temperature raising of 10° C./min).
Heat of fusion; according to DSC determination
Further, the calculated values of C$_4$H$_6$O$_2$ in the elementary analysis are as follows:

| C | H |
|---|---|
| 55.81% | 7.02% |

EXAMPLE 14

The same procedure as in EXAMPLE 13 was repeated except for using sodium 4-hydroxybutyrate (20 g/liter) as the carbon source in the latter stage of culture. The results are shown in TABLE 3.

EXAMPLE 15

The same procedure as in EXAMPLE 10 was repeated except for using *Alcaligenes eutrophs* NCIB 11599. The results are shown in TABLE 3.

TABLE 3

| | Weight of dried fungus (g) | Content of copolyester (%) | Composition of copolyester (mol %) | | Chain distribution (mol %) | | | | [η] (dl/g) | Melting temperature (°C.) | Heat of fusion (cal/g) | Elementary analysis (%) | | |
|---|---|---|---|---|---|---|---|---|---|---|---|---|---|---|
| | | | 3 HB | 4 HB | [3 HB-3 HB] | [3 HB-4 HB] | [4 HB-3 HB] | [4 HB-4 HB] | | | | C | H | Cl |
| Example 13 | 5.1 | 27 | 89 | 11 | 82 | 9 | 9 | 0 | 3.9 | 156 | 11.1 | 55.50 | 7.09 | 0.29 |
| Example 14 | 3.7 | 30 | 67 | 33 | 55 | 13 | 13 | 19 | 2.9 | 166 | 3.7 | 55.60 | 6.64 | — |
| Example 15 | 4.5 | 20 | 51 | 49 | 32 | 21 | 19 | 28 | 6.1 | 159 | 0.5 | 55.18 | 6.95 | — |
| Comparative Example 1 | 9.5 | 51 | 100 | — | 100 | 0 | 0 | 0 | 3.3 | 177 | 19.5 | 55.88 | 7.34 | — |

EXAMPLES 16 TO 19 AND COMPARATIVE EXAMPLES 3 TO 4

Figure 5:
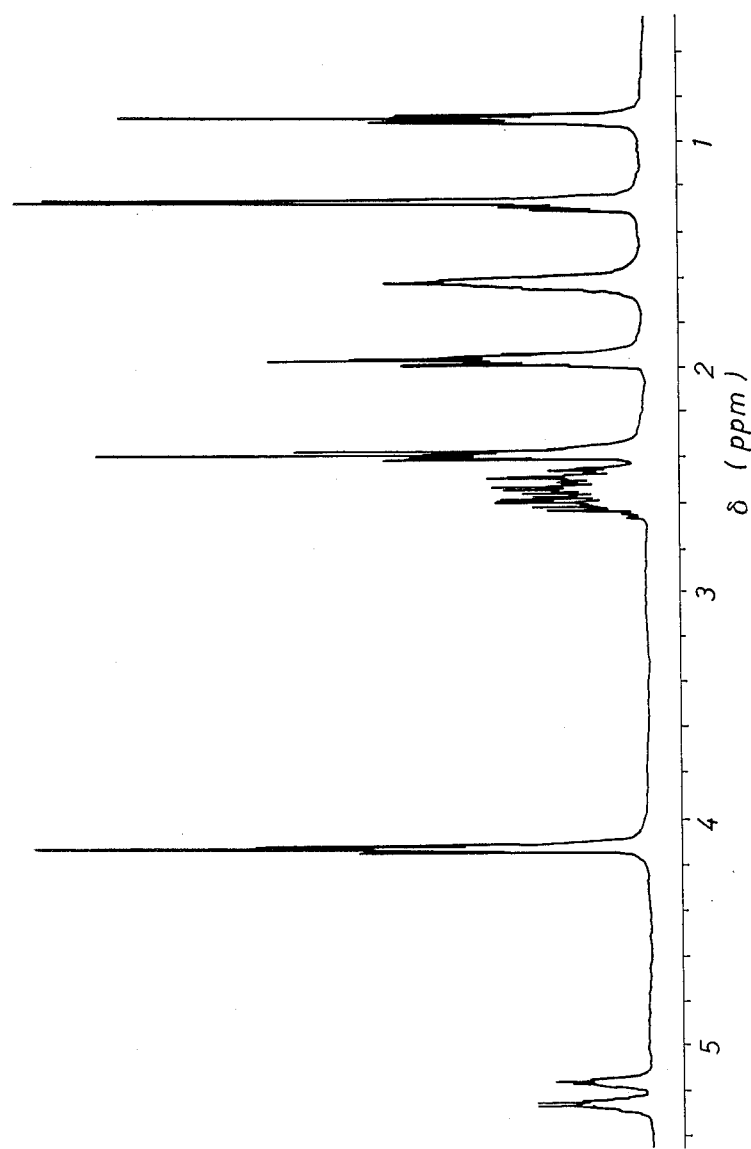
Figure 6:
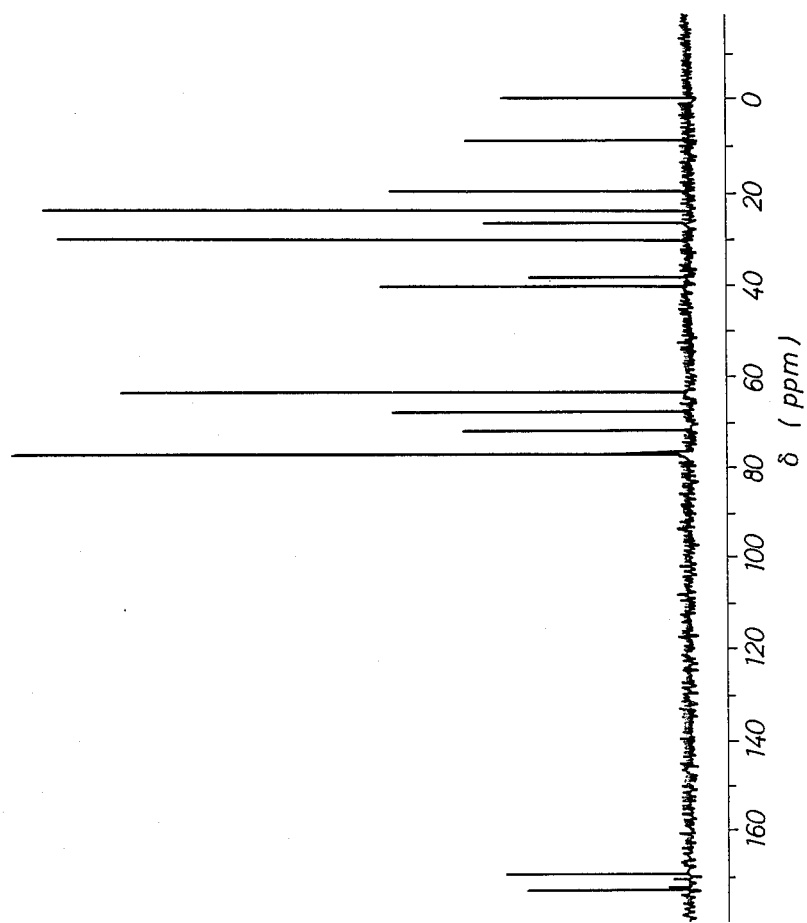

By the same procedure as in EXAMPLE 1 except for using the compound shown in TABLE 4 as the carbon source in the latter stage of culture, the copolyesters were produced, and the properties thereof were measured. The results are shown in TABLE 4. Further, the $^1$H-NMR spectrum at 500 MHz of the copolyester obtained in EXAMPLE 16 was shown in FIG. 5, and the $^{13}$C-NMR spectrum at 125 MHz of the same was shown in FIG. 6.

TABLE 4

| | Carbon source (g) | | Weight of dried fungus (g) | Content of copolyester (% by weight) | Composition of copolyester (mol %) | | | [η] (dl/g) | Melting temperature (°C.) | Heat of fusion (cal/g) |
|---|---|---|---|---|---|---|---|---|---|---|
| | 4-hydroxy butyric acid | valeric acid | | | [3 HB] | [4 HB] | [3 HV] | | | |
| Example 16 | 17.5 | 2.5 | 7.8 | 18 | 32 | 45 | 23 | 3.7 | 166 / 87 / 78 | 3.1 / 2.3 |
| Example 17 | 15.0 | 5.0 | 9.6 | 17 | 34 | 30 | 36 | 5.7 | 163 / 89 / 81 | 2.5 / 3.3 |
| Example 18 | 10.0 | 10.0 | 10.4 | 24 | 31 | 14 | 55 | 6.4 | 162 / 92 | 1.6 / 4.8 |
| Example 19 | 7.5 | 12.5 | 10.5 | 24 | 28 | 5 | 67 | 7.1 | 171 / 94 | 1.4 / 8.1 |
| Comparative Example 3 | 20 | 0 | 7.2 | 19 | 66 | 34 | 0 | 4.0 | 166 | 7.1 |
| Comparative Example 4 | 0 | 20 | 12.5 | 36 | 10 | 0 | 90 | 4.0 | 108 | 13.8 |

EXAMPLES 20 TO 24 AND COMPARATIVE EXAMPLES 5 TO 7

By the same procedure as in EXAMPLE 4 except for using the compound shown in TABLE 5 as the carbon source in the latter stage of culture, the copolyesters were produced, and the properties thereof were measured. The results are shown in TABLE 5.

Figure 7:
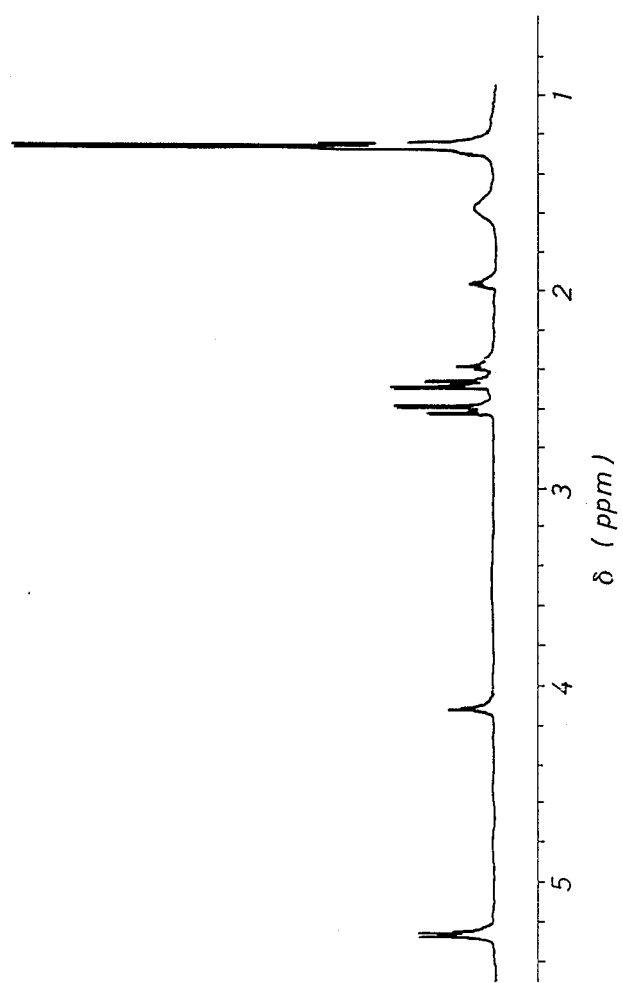
Figure 8:
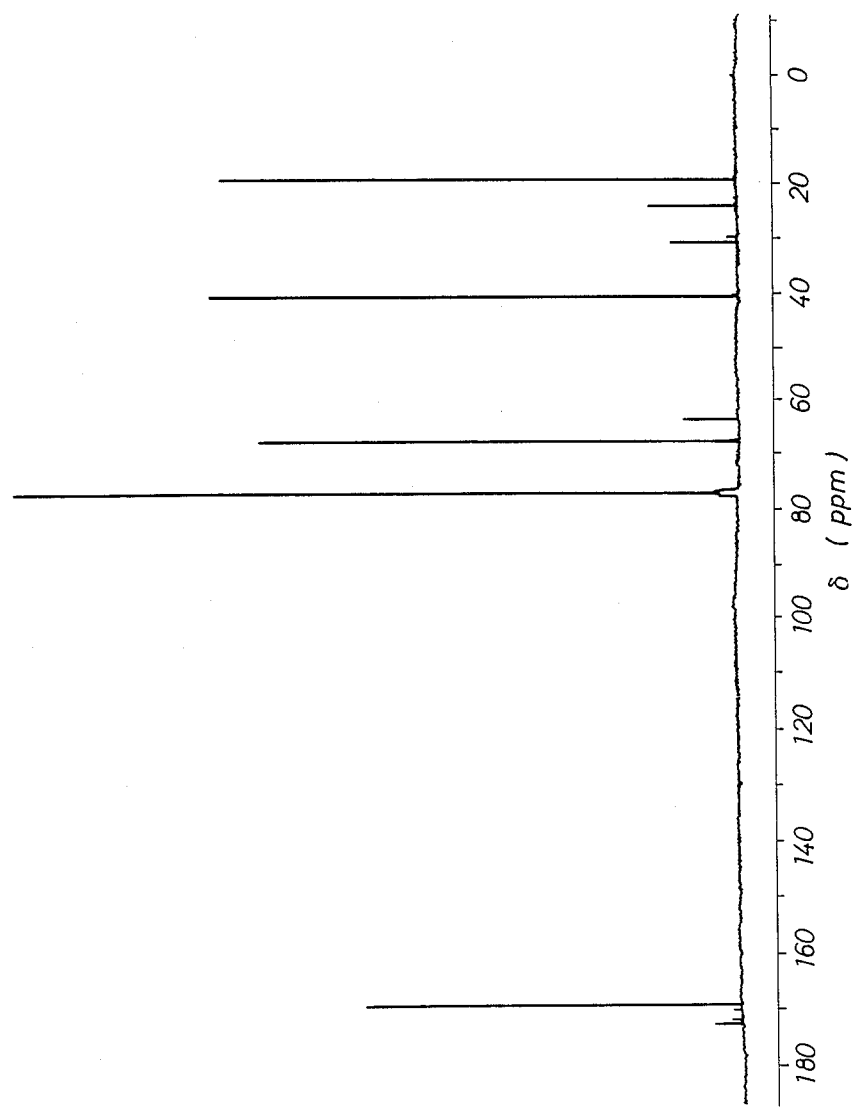
Figure 9:
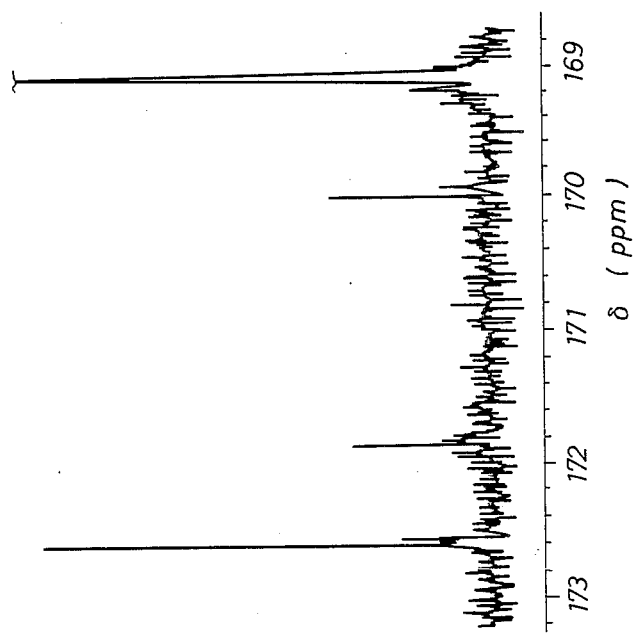
FIG. 9 is an enlarged spectrum of the spectrum on FIG. 8.

Further, the $^1$H-NMR spectrum at 500 MHz of the copolyester obtained in EXAMPLE 21 was shown in FIG. 7, and the $^{13}$C-NMR spectrum at 125 MHz of the same and an enlarged spectrum thereof were shown in FIGS. 8 and 9, respectively.

TABLE 5

| | Carbon source (g) | | Weight of dried fungus (g) | Content of copolyester (% by weight) | Composition of copolyester (mol %) | | | [η] (dl/g) |
|---|---|---|---|---|---|---|---|---|
| | | | | | 3 HB | 4 HB | 3 HV | |
| Example 20 | 1,4-butanediol | 20 | 2.66 | 8 | 75 | 25 | 0 | — |
| Example 21 | 1,4-butanediol Butyric acid | 17 3 | 3.91 | 34 | 83 | 17 | 0 | 2.9 |
| Example 22 | 1,4-butanediol Butyric acid | 13 7 | 5.05 | 52 | 93 | 7 | 0 | 2.8 |
| Example 23 | 1,4-butanediol Butyric acid | 10 10 | 6.20 | 63 | 97 | 3 | 0 | 3.6 |
| Example 24 | 1,4-butanediol Butyric acid | 5 15 | 4.60 | 47 | 99 | 1 | 0 | 2.9 |

TABLE 5-continued

|  | Carbon source (g) | Weight of dried fungus (g) | Content of copolyester (% by weight) | Composition of copolyester (mol %) | | | [η] (dl/g) |
|---|---|---|---|---|---|---|---|
|  |  |  |  | 3 HB | 4 HB | 3 HV |  |
| Comparative Example 5 | 1,3-propanediol 20 | 3.70 | 3 | 94 | 0 | 6 | — |
| Comparative Example 6 | 1,5-pentanediol 20 | 3.52 | 4 | 95 | 0 | 5 | — |
| Comparative Example 7 | Butyric acid 20 | 4.80 | 51 | 100 | 0 | 0 | 3.3 |

EXAMPLES 25 TO 29 AND COMPARATIVE EXAMPLES 8 TO 9

By the same procedure as in EXAMPLE 1 except for using *Alcaligenes eutrophs* H-16 ATCC 17699 and using the compound shown in TABLE 6 as the carbon source in the latter stage of culture, the copolyesters were produced, and the properties thereof were measured. The results are shown in TABLE 6.

TABLE 6

|  | Carbon source (g) | | | Weight of dried fungus (g) | Content of copolyester (% by weight) | Composition of copolyester (mol %) | | [η] (dl/g) | Melting temperature (°C.) | Heat of fusion (cal/g) |
|---|---|---|---|---|---|---|---|---|---|---|
|  | γ-butyro-lactone | Butyric acid | 4-Hydroxy butyric acid |  |  | 3 HB | 4 HB |  |  |  |
| Example 25 | 2.0 | — | — | 0.81 | 6 | 90 | 10 | 3.3 | 169 | 12 |
| Example 26 | 0.5 | 1.5 | — | 1.24 | 28 | 95 | 5 | 3.4 | 165 | 19 |
| Example 27 | 1.0 | 1.0 | — | 1.03 | 22 | 93 | 7 | — | 165 | 18 |
| Example 28 | 1.5 | 0.5 | — | 0.80 | 8 | 89 | 11 | — | 170 | 13 |
| Example 29 | 10 | 10 | — | 7.50 | 42 | 73 | 27 | 2.7 | 168 | 9 |
| Comparative Example 8 | — | 2.0 | — | 1.58 | 36 | 100 | 0 | 3.3 | 175 | 18 |
| Comparative Example 9 | — | 10 | 10 | 7.90 | 28 | 71 | 29 | 2.7 | 167 | 10 |

What is claimed is:

1. A copolyester comprising a 3-hydroxybutyrate unit and one selected from the group consisting of (1) a 3-hydroxyvalerate unit and a 5-hydroxyvalerate unit, (2) a 4-hydroxybutyrate unit and (3) a 4-hydroxybutyrate unit and a 3-hydroxyvalerate unit, the intrinsic viscosity of said copolyester being in the range of 0.4 to 10.0 dl/g in chloroform at 30° C.

2. The copolyester according to claim 1, which comprises 2 to 50 mol% of 3-hydroxybutyrate unit, 3 to 95 mol% of 3-hydroxyvalerate unit and 3 to 90 mol% of 5-hydroxyvalerate unit.

3. The copolyester according to claim 1, which comprises 40 to 97 mol% of 3-hydroxybutyrate unit and 3 to 60 mol% of 4-hydroxybutyrate unit.

4. The copolyester according to claim 1, which comprises 10 to 90 mol% of 3-hydroxybutyrate unit, 3 to 60 mol% of 4-hydroxybutyrate unit and 5 to 87 mol% of 3-hydroxyvalerate unit.

* * * * *